United States Patent [19]

Sheth et al.

[11] 4,424,235

[45] Jan. 3, 1984

[54] HYDRODYNAMICALLY BALANCED CONTROLLED RELEASE COMPOSITIONS CONTAINING L-DOPA AND A DECARBOXYLASE INHIBITOR

[75] Inventors: Prabhakar R. Sheth, Pearl River, N.Y.; Jacques L. Tossounian, Pine Brook, N.J.

[73] Assignee: Hoffmann-La Roche Inc., Nutley, N.J.

[21] Appl. No.: 438,205

[22] Filed: Nov. 1, 1982

Related U.S. Application Data

[63] Continuation of Ser. No. 301,498, Sep. 14, 1981, abandoned.

[51] Int. Cl.³ .............................................. A61K 31/195
[52] U.S. Cl. ..................................................... 424/319
[58] Field of Search ......................................... 424/319

[56] References Cited

U.S. PATENT DOCUMENTS 3,557,292  1/1971  Bartholini .......................... 424/319

*Primary Examiner*—Stanley J. Friedman
*Attorney, Agent, or Firm*—Jon S. Saxe; George M. Gould; John J. Maitner

[57] ABSTRACT

Hydrodynamically balanced controlled release compositions for the preparation of pharmaceutical capsules or tablets which contain L-Dopa and a decarboxylase inhibitor and which provide superior blood levels of L-Dopa are disclosed.

20 Claims, No Drawings

HYDRODYNAMICALLY BALANCED CONTROLLED RELEASE COMPOSITIONS CONTAINING L-DOPA AND A DECARBOXYLASE INHIBITOR

This is a continuation of application Ser. No. 301,498 filed Sept. 14, 1981, now abandoned.

BACKGROUND OF THE INVENTION

L-Dopa, (−)-3-(3,4-dihydroxyphenyl)-L-alanine, is a known compound which is important in the therapeutic treatment of Parkinsonism.

Many of the decarboxylase inhibitors are also known compounds. For example, $N^1$-dl-seryl-$N^2$-(2,3,4-trihydroxybenzyl)-hydrazine hydrochloride is disclosed in Hegedus et al. U.S. Pat. No. 3,178,476, and is effective as a decarboxylase inhibitor.

The use of a combination of L-Dopa and a specific decarboxylase inhibitor, $N^1$-dl-seryl-$N^2$-(2,3,4-trihydroxybenzyl)-hydrazine hydrochloride, in the treatment of Parkinsonism is disclosed in Bartholini et al. U.S. Pat. No. 3,557,292.

The use of L-Dopa alone in a rapidly disintegrating tablet is disclosed in Sheth et al. U.S. Pat. No. 3,632,778.

Heretofore, large amounts of L-Dopa had to be used in the treatment of Parkinsonism since much of the administered L-Dopa is metabolized by enzymes, i.e. decarboxylases, in the stomach or blood before the L-Dopa passes the blood-brain barrier where its therapeutic activity is utilized.

The amount of orally administered L-Dopa crossing the blood-brain barrier intact can be materially increased, i.e. the anti-Parkinson activity is "potentiated", if the L-Dopa is administered in combination with a known decarboxylase inhibitor.

However, regular capsule and tablet formultions containing L-Dopa and a decarboxylase inhibitor, while initially showing higher blood levels of L-Dopa, do not sustain such blood levels beyond an initial peak which is similar to that obtained when L-Dopa is administered alone.

Conventional controlled release formulations containing L-Dopa do not lead to the desired therapeutic response, i.e. high blood levels of L-Dopa.

In accordance with this invention, it has been found that hydrodynamically balanced controlled release formulations containing both L-Dopa and a decarboxylase inhibitor provide superior blood levels of L-Dopa.

DETAILED DESCRIPTION OF THE INVENTION

This invention is based on the discovery that the oral administration of hydrodynamically balanced controlled release capsules or tablets containing both L-Dopa and a decarboxylase inhibitor not only significantly increases the level of L-Dopa in the blood but also results in more sustained blood levels of L-Dopa than from either regular capsules or tablets containing both L-Dopa and a decarboxylase inhibitor or from conventional controlled release capsules or tablets containing either L-Dopa alone or a combination of L-Dopa and a decarboxylase inhibitor.

The oral administration of L-Dopa and decarboxylase inhibitor from a controlled release formulation is improved by a hydrodynamically balanced capsule or tablet dosage form.

In the controlled release compositions used in the practice of this invention, the dosage forms either as capsules or tablets remain buoyant and freely floating in the gastric fluid for an extended period of time during which substantially all of the active ingredients contained in the formulations are released in the gastric fluid.

Formulations which remain intact and buoyant in the gastric fluid while substantially all of the medicament is released therefrom are described in the art. See, for example, U.S. Pat. Nos. 4,126,672; 4,140,755 and 4,167,558 where formulations for the preparation of controlled release capsules and tablets for oral administration are described. The capsules and tablets are hydrodynamiclly balanced to have a bulk density (specific gravity) of less than one in contact with gastric fluid and, therefore, will remain floating in gastric fluid which has a specific gravity of between 1.004 and 1.010. These controlled release formulations comprise a mixture of the active ingredients with one or more hydrophilic hydrocolloids.

Upon oral ingestion of the controlled release capsule or tablet, the capsule shell or the tablet coating, whichever is present, dissolves and the formulation comes in contact with gastric fluid. The outermost hydrocolloid hydrates forming, in effect, an outside barrier causing the capsule or tablet to enlarge somewhat and preventing water permeation. Buoyancy results from the combination of this increase in bulk volume of the dosage form and the center voids in the capsule or tablet remaining dry as a result of the aforesaid barrier. The resulting soft gelatinous mass acquires and maintains a bulk density of less than one. As the hydrated outermost layer slowly dissolves, L-dopa and the decarboxylase inhibitor are slowly released therefrom by diffusion and/or by erosion. Subsequently, new hydrated outer layers form from the now-exposed hydrocolloids thus maintaining the integrity of the barrier. The process is continuous, with the dosage form remaining buoyant in gastric fluid, until all medicaments are substantially leached out. The remaining matrix, which is still buoyant in gastric fluid, is slowly dispersed or eliminated.

The release pattern and the resulting blood levels attained with these controlled release formulations have advantages over the conventional controlled release mechanisms.

Decarboxylase inhibitors function by inhibiting decarboxylase activity and, thus, lead to an increase in the concentration of administered L-Dopa in the plasma. Many such decarboxylase inhibitors are known. Among these known decarboxylase inhibitors suitable for use in these hydrodynamically balanced, controlled release formulations are:

$N^1$—dl-seryl-$N^2$—(2,3,4-trihydroxybenzyl)hydrazine hydrochloride, (a)

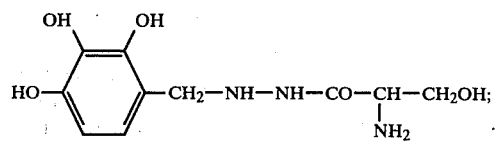

β-(3,4-dihydroxyphenyl)-α-hydrazino-α-methyl propionic acid, (b)

-continued

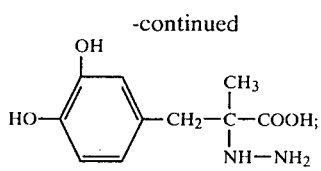

m-hydroxybenzylhydrazine, (c)

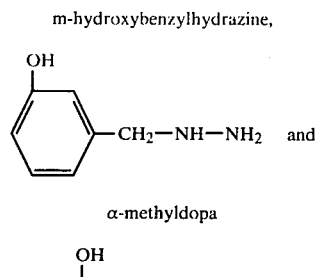

α-methyldopa (d)

$N^1$-dl-seryl-$N^2$-(2,3,4-trihydroxybenzyl)-hydrazine hydrochloride is the preferred decarboxylase inhibitor of this invention.

Hydrocolloids suitable for use in these controlled release formulations include one or more natural, partially or totally synthetic anionic or, preferably, nonionic hydrophilic gums, modified cellulosic substances or proteinaceous substances such as, for example, acacia, gum tragacanth, locust bean gum, guar gum, karaya gum, agar, pectin, carrageen, soluble and insoluble alginates, methylcellulose, hydroxy-propyl methylcellulose, hydroxypropylcellulose, sodium carboxymethylcellulose, carboxypolymethylene (Carbopol-Cabot Corporation), gelatin, casein, zein, bentonite, Veegum (R. T. Vanderbilt Co.) and the like. A preferred hydrocolloid is hyroxypropyl methylcellulose. The use of such materials in pharmaceutical compounding is also known in the art. For example, Kaplan et al. U.S. Pat. No. 3,555,151 discloses the use of such hydrocolloids in sustained release antacid preparations.

The hydrocolloids utilized must hydrate in acidic medium, i.e., gastric fluid with a pH equivalent to 0.1N hydrochloric acid (pH of approximately 1.2). Furthermore, although the initial bulk density of certain formulations contained in the controlled release preparations of the invention, and, in particular, tablets, may be greater than one, it is essential that the formulation be hydrodynamically balanced to have a bulk density of less than one when in contact with gastric fluids to assure buoyancy. There are a number of methods whereby the rate of release of medication from a controlled release formulation can be adjusted. First, the choice of a particular hydrocolloid or mixture of hydrocolloids can affect the release rate, e.g., high viscosity hydrocolloids, e.g., hydroxypropyl methylcellulose, 4000 cps, hydrate more slowly and maintain a soft mass for a longer time than low viscosity hydrocolloids, e.g., hydroxypropyl methylcellulose, 10 cps. Further, edible, pharmaceutically inert, fatty materials having a specific gravity of less than one can be added to the formulation to decrease the hydrophilic property of the formulation and therefore increase buoyancy. Examples of such materials include a purified grade of beewax; fatty acids; long chain fatty alcohols such as, for example, cetyl alcohol, stearyl alcohol; esters of fatty acids such as, for example, glyceryl monostereate; hydrogenated castor oil and the like.

There may also be incorporated in these controlled release formulations additional edible nontoxic ingredients recognized in the art of pharmaceutical compounding such as excipients, i.e., buffering agents, preservatives, stabilizers, tabletting lubricants and the like.

The amount of hydrocolloid ingredient present in these controlled release formulations may vary within a wide range, i.e., from about 5% by weight to about 80% by weight. The amount of hydrocolloid will vary in relation to the amounts and properties of the active ingredient and inert pharmaceutical adjuncts utilized. Generally, the amount of hydrocolloid will be between about 15% by weight and about 60% by weight.

When a fatty material or a mixture of fatty materials is present in the controlled release formulations, such material comprises up to about 60% by weight of the total formulation. In general, when the formulations contain a fatty material, such material is present in from about 5% by weight to about 30% by weight. The amount of fatty material is governed by the amounts and physical characteristics of both the active ingredient and the hydrocolloid with the object being to achieve a hydrodynamically balanced formulation, i.e., a formulation which acquires a bulk density of less than one in gastric fluids.

The amount of edible inert pharmaceutical adjunct materials which may be present in the controlled release formulations will also vary in accordance with the amounts and physical properties of the other ingredients. Such materials which themselves have a bulk density of less than one, e.g., ethylcellulose or other bulking agent, will enhance the buoyancy of the formulation. Small amounts of carbon dioxide generating agents can also be utilized in the formulation to enhance buoyancy as long as the density of the dosage form is not too high. When such substances generate carbon dioxide, bubbles will become entrapped by the hydrated outer layer and, thus, enhance the buoyancy of the formulation. More importantly, it is possible to utilize the selection of inert pharmaceutical adjunct materials to modify the rate of release of the active ingredients from the formulation. For example, soluble excipients, e.g., lactose, mannitol and the like, will increase the rate of release whereas insoluble excipients, e.g., dicalcium phosphate, terra alba and the like, will decrease the rate of release. When such pharmaceutical adjunct materials are included in the formulations, they can be present in up to about 80% by weight of the final formulation. Generally, such conventional pharmaceutical adjuncts are present in from about 5% by weight to about 60% by weight of the formulation. The inclusion of and choice of such materials is again considered to be within the purview of the art.

The hydrodynamically balanced controlled release capsule or tablet compositions can contain from about 10% by weight to about 70% by weight of L-Dopa and, preferably, about 20% to about 50% by weight.

The amount of decarboxylase inhibitor in the hydrodynamically balanced controlled release capsule or tablet compositions is dependent on the particular inhibitor used. The effective range is from about 2% to about 20% by weight and, preferably, from about 4% to about 10% by weight.

The preferred decarboxylase inhibitor in the practice of this invention is $N^1$-dl-seryl-$N^2$-(2,3,4-trihydroxybenzyl)-hydrazine hydrochloride. The amount of $N^1$-dlseryl-$N^2$-(2,3,4-trihydroxybenzyl)-hydrazine hydrochloride in the hydrodynammically balanced controlled release capsule or tablet compositions can range from about 3% by weight to about 15% by weight and, preferably is about 4% by weight to about 10% by weight.

Factors which influence the amounts of active ingredients present in these controlled release formulations include the amount needed for full therapeutic dose, the bulk density of the active ingredients, the hydrophilic or hydrophobic properties of the active ingredients, the stability and the like. These properties are known and are easily ascertained by a person skilled in the art.

The ratio of L-Dopa to decarboxylase inhibitor can vary from about 10 parts of L-Dopa to about 3 parts of L-Dopa for each part by weight of decarboxylase inhibitor.

The ratio of L-Dopa to $N^1$-dl-seryl-$N^2$-(2,3,4-trihydroxybenzyl)-hydrazine hydrochloride can also vary considerably. The ratio is about 5 parts to about 3 parts by weight of L-Dopa for each part by weight of decarboxylase inhibitor. The preferred ratio is about 4:1.

The hydrodynamically balanced controlled release formulations are prepared by techniques well established in the art. In most instances, all that is required is the thorough mixing of all ingredients to form a homogeneous mixture and milling or comminuting the mixture to a relatively fine particle size, i.e., all particles passing a 100 mesh screen. Milling the mixture to a very fine particle size, and, in particular, the hydrocolloids, does not detract from the controlled release mechanism and, in fact, exerts a positive effect thereon. Under certain circumstances the conventional pharmaceutical techniques of slugging, wet granulating or extruding may be required to achieve proper fill weight in the capsule or to prepare the tablet. However, it is essential that the hydrocolloids should not be entrapped within any granulations to avoid subsequent difficulty in their hydration when in contact with gastric fluid. For capsules, it is preferred to comminute the mixture to a fine particle size and completely fill the capsule.

For tablets, the ingredients are, preferably, granulated and the composition is then compressed into tablets. Tablets can be manufactured on conventional tabletting equipment. However, the tablets should not be compressed to such a degree of hardness that they will not acquire a bulk density of less than one when in contact with gastric fluid. Therefore, the hardness of the tablets is critical and depends on the initial density of the formulation and the size of the tablet.

The following Examples illustrate the invention.

EXAMPLE 1

Formulation A.

Hydrodynamically balanced, controlled release capsules were prepared from the following formulation:

| Ingredient | Mg./capsule |
|---|---|
| $N^1$—dl-seryl-$N^2$—(2,3,4-trihydroxybenzyl)-hydrazine hydrochloride | 29.63 |
| L-Dopa | 102.00 |
| Monocalcium phosphate | 24.37 |
| Hydrogenated cottonseed oil | 30.00 |
| Hydroxypropylcellulose | 4.00 |
| Mannitol | 20.00 |
| Hydroxypropyl methylcellulose | 115.00 |
| Talc | 15.00 |
| | 340.00 |

The $N^1$-dl-seryl-$N^2$-(2,3,4-trihydroxybenzyl)-hydrazine hydrochloride, L-Dopa, monocalcium phosphate and hydrogenated cottonseed oil were mixed and milled. This powder mix was then granulated with hydroxypropylcellulose dissolved in alcohol. Mannitol and hydroxypropyl methylcellulose were then mixed and milled and the powder mix was added to the granulate. The resulting granulate mix was dried, mixed with the talc lubricant and filled into capsules.

Formulation B.

Regular capsules were prepared from the following formulation:

| Ingredient | Mg/capsule |
|---|---|
| $N^1$—dl-seryl-$N^2$—(2,3,4-trihydroxybenzyl)-hydrazine hydrochloride | 29.91 |
| L-Dopa | 101.00 |
| Polyvinyl pyrrolidone | 1.00 |
| Methylene chloride | qs |
| Microcrystalline cellulose | 13.50 |
| Talc | 6.50 |
| Magnesium stearate | 6.50 |
| | 152.41 |

The $N^1$-dl-seryl-$N^2$-(2,3,4-trihydroxybenzyl)-hydrazine hydrochloride and L-Dopa are mixed and milled. This powder mixture is then granulated with the polyvinyl pyrrolidone in methylene chloride. The granulate is dried and the granules are milled. The microcrystalline cellulose, talc and magnesium stearate are added. The composition is mixed thoroughly and poured into capsules.

Formulation C.

Hydrodynamically balanced, controlled release tablets were prepared from the following formulation:

| Ingredient | Mg/tablet |
|---|---|
| L-Dopa | 204.00 |
| Mannitol | 23.00 |
| Calcium carbonate | 50.00 |
| Carboxymethyl cellulose | 50.00 |
| Polyvinyl pyrrolidone | 10.00 |
| Hydroxypropyl methylcellulose | 110.00 |
| $N^1$—dl-seryl-$N^2$—(2,3,4-trihydroxybenzyl)-hydrazine hydrochloride | 58.00 |
| Fumaric acid | 25.00 |
| Talc | 12.00 |
| Magnesium stearate | 3.00 |
| | 545.00 |

The L-Dopa, mannitol, calcium carbonate and carboxymethylcellulose were granulated with part of the polyvinyl pyrrolidone in alcohol. The hydroxypropyl methylcellulose was added to the granulate which was then dried overnight.

$N^1$-dl-seryl-$N^2$-(2,3,4-trihydroxybenzyl)-hydrazine hydrochloride was mixed with fumaric acid and granulated with the remaining polyvinyl pyrrolidone in alcohol. The granulate was then dried.

The L-Dopa granulation and the $N^1$-dl-seryl-$N^2$-(2,3,4-trihydroxybenzyl)-hydrazine hydrochloride granulation were mixed with the talc and magnesium stearate. Quantitative amounts of each were compressed together on ½ S. C. punches at a hardness of 5–8 SCU. Hardness should not exceed 12 SCU.

EXAMPLE 2

In Vitro Studies

The hydrodynamically balanced controlled release formulations of Example 1 in capsule and tablet forms, as well as the regular capsule from Example 1, are evaluated below for in vitro release of L-Dopa and $N^1$-dl-seryl-$N^2$-(2,3,4-trihydroxybenzyl)-hydrazine hydrochloride.

Capsules and tablets are individually placed in 60 ml of gastric fluid in a bottle and rotated at 20 rpm. The fluid used is at a pH of 1.2 (the normal pH of gastric fluid). Samples were removed at certain time intervals and assayed spectrophotometrically for L-Dopa and $N^1$-dl-seryl-$N^2$-(2,3,4-trihydroxybenzyl)-hydrazine hydrochloride.

The table below lists the results of in vitro release. The letters under the heading "Formulation" correspond to the letter used for the particular formulation in Example 1.

| Formulation | Time, hours | % Released L-Dopa | Decarboxylase Inhibitor |
|---|---|---|---|
| A | 0.50 | 37 | 40 |
| (hydrodynamically | 1.00 | 63 | 65 |
| balanced, controlled | 2.00 | 94 | 95 |
| release capsule) | | | |
| B | 0.25 | 102 | 89 |
| (regular capsule) | | | |
| C | 0.50 | 26 | 32 |
| (hydrodynamically | 1.00 | 80 | 91 |
| balanced, controlled | 2.00 | 105 | 107 |
| release tablet) | | | |

In Vivo Studies

The bioavailability of L-Dopa was determined following administration to humans of either regular capsules (Formulation B of Example 1) or hydrodynamically balanced controlled release capsules (Formulation A of Example 1), each containing 100 mg of L-Dopa and 25 mg of $N^1$-dl-seryl-$N^2$-(2,3,4,trihydroxybenzyl)-hydrazine.

The relative bioavailabilities of the formulations were determined using five male subjects. Formulations were administered with 100 ml of water after an overnight fast.

Blood samples of the subjects were collected, into heparinized tubes, immediately before dose administration, five times during the first two hours after administration and then at hourly intervals for 9–10 hours.

L-Dopa concentration in the blood was measured by a modification of the method of Spiegel and Tonchen. (Spiegel, H. E. and Tonchen, A. E. (1970): Semiautomated method for measurement of dopa in plasma, Clin. Chem. 16,763.

Samples were compared with blood plasma standards. Results are

| | 2 × (100 + 25) mg capsules | | 4 × (100 + 25) mg capsules | |
|---|---|---|---|---|
| Plasma L-Dopa | Regular | Cont. Rel. | Regular | Cont. Rel. |
| Peak concentration, ug/ml | 1.9 | 0.97 | — | 2.6 |
| Time to peak concentration, hours | 1.1 | 2.9 | — | 2.6 |
| Area under curve ug/hr/ml$^{-1}$ | 3.2 | 2.0 | — | 10.1 |

Blood plasma level data were compared with a standard preparation. For the 2×(100+25) mg dosage rate, there was a difference between the controlled release and the regular formulations. The high peaks of L-Dopa concentration in the blood which resulted with the regular capsules did not occur with the hydrodynamically balanced controlled release capsules. The peak time was delayed from 1.1 hours for regular capsules to 2.9 hours for the controlled release capsules indicating a slower rate of absorption.

At the higher dosage [4×(100+25) mg], the area under the plasma level/time concentration curve was disproportionately greater than seen after the 2×2×(100+25) mg dose.

(200+50) mg Controlled Release Capsule Area Under Curve 2±0.2 ug/hr/ml$^{-1}$ (400+100) mg Controlled Release Capsule Area Under Curve 10±1.5 ug/hr/ml$^{-1}$ Patients on regular capsules could not tolerate the 400 mg dose (e.g. gastric upset).

We claim:

1. A hydrodynamically balanced controlled release composition comprising (a) as the active ingredient, an amount of L-Dopa which is effective in achieving desired levels of L-Dopa in the blood and an amount of a decarboxylase inhibitor selected from the group consisting of $N^1$-dl-seryl-$N^2$-(2,3,4-trihydroxybenzyl) hydrazine hydrochloride, $\beta$-(3,4-dihydroxyphenyl)-$\alpha$-hydrazino-$\alpha$methyl propionic acid, m-hydroxybenzylhydrazine and $\beta$-methyldopa, which is effective for the amount of L-Dopa in the composition and wherein the ratio of L-Dopa to decarboxylase inhibitor ranges from about 4:1 to about 10:1 and, (b) in percents by weight based on the total weight of the composition, from about 5% to about 80% of a hydrocolloid or mixture of hydrocolloids selected from the group consisting of acacia, gum tragacanth, locust bean gum, guar gum, karaya gum, agar, pectin, carrageen, soluble and insoluble alginates, methylcellulose, hydroxy-propyl methylcellulose, hydroxypropylcellulose, sodium carboxymethylcellulose, carboxypolymethylene, gelatin, casein, zein and bentonite; up to about 60% of a fatty material or mixture of fatty materials selected from the group consisting of beeswax, cetyl alcohol, stearyl alcohol, glycerylmonostearate, hydrogenated caster oil and hydrogenated cottonseed oil and up to about 80% of edible inert pharmaceutical adjunct materials whereby said composition, when used in capsule or tablet form, is hydrodynamically balanced so that, upon contact with gastric fluid, said capsule or tablet acquires and maintains a bulk density of less than one thereby being buoyant in the gastric fluid and remaining buoyant in the gastric fluid of the stomach until substantially all of the active ingredients contained therein have been released.

2. A hydrodynamically balanced controlled release composition comprising (a) as the active ingredient, an amount of L-Dopa which is effective in achieving desired levels of L-Dopa in the blood and an amount of $N^1$-dl-seryl-$N^2$-(2,3,4-trihydroxybenzyl)-hydrazine hydrochloride which is effective as a decarboxylase inhibitor for the L-Dopa in the composition and wherein the ratio of L-Dopa to $N^1$-dl-seryl-$N^2$-(2,3,4-trihydroxybenzyl-hydrazine ranges from about 5:1 to about 3:1 and, (b) in percents by weight based on the total weight of the composition from about 5% to about 80% of a hydrocolloid or mixture of hydrocolloids selected from the group consisting of acacia, gum tragacanth, locust bean gum, guar gum, karaya gum, agar, pectin, carrageen, soluble and insoluble alginates, methylcellulose, hydroxy-propyl methylcellulose, hydroxypropylcellulose, sodium carboxymethylcellulose, carboxypolymethylene, gelatin, casein, zein and bentonite; up to about 60% of a fatty material or mixture of fatty materials, selected from the group consisting of beeswax, cetyl alcohol, stearyl alcohol, glyceryl monosteareate, hydrogenated caster oil and hydrogenated cottonseed oil and up to about 80% of edible inert pharmaceutical adjunct materials whereby said composition, when used in capsule or tablet form, is hydrodynamically balanced so that, upon contact with gastric fluid, said capsule or tablet acquires and maintains a bulk density of less than one thereby being buoyant in the gastric fluid and remaining buoyant in the gastric fluid of the stomach until substantially all of the active ingredients contained therein have been released.

3. The hydrodynamically balanced controlled release composition of claim 1 which comprises, in percents by weight based on the total weight of the composition, (a) from about 20% to about 50% of L-Dopa;

(b) from about 2% to about 20% of a decarboxylase inhibitor;

(c) from about 15% to about 60% of hydrocolloid;

(d) up to about 30% of a fatty material or mixture of fatty materials and (e) from about 5% to about 60% of edible inert pharmaceutical adjunct materials and wherein the ratio of L-Dopa to decarboxylase inhibitor is from about 4:1 to about 10:1.

4. The hydrodynamically balanced controlled release composition of claim 2 which comprises, in percents by weight based on the total weight of the composition, (a) from about 20% to about 50% of L-Dopa;

(b) from about 4% to about 10% of $N^1$-dl-seryl-$N^2$-(2,3,4-trihydroxybenzyl)-hydrazine hydrochloride;

(c) from about 15% to about 60% of a hydrocolloid;

(d) up to about 30% of a fatty material or mixture of fatty materials and (e) from about 5% to about 60% of edible inert pharmaceutical adjunct materials and wherein the ratio of L-Dopa to $N^1$-dl-seryl-$N^2$-(2,3,4-trihydroxybenzyl)-hydrazine hydrochlorine is about 4:1.

5. The hydrodynamically balanced controlled release composition of claim 1 wherein the hydrocolloid or mixture of hydrocolloids is selected from the group consisting of methylcellulose, hydroxypropylcellulose, hydroxypropyl methylcellulose, sodium carboxymethylcellulose and carboxypolymethylene.

6. The hydrodynamically balanced controlled release composition of claim 2 wherein the hydrocolloid or mixture of hydrocolloids is selected from the group consisting of methylcellulose, hydroxypropylcellulose, hydroxypropyl methylcellulose, sodium carboxymethylcellulose and carboxypolymethylene.

7. The hydrodynamically balanced controlled release composition of claim 3 wherein the hydrocolloid is hydroxypropyl methylcellulose.

8. The hydrodynamically balanced controlled release composition of claim 4 wherein the hydrocolloid is hydroxypropyl methylcellulose.

9. A hydrodynamically balanced controlled release capsule dosage form prepared from the composition of claim 1.

10. A hydrodynamically balanced controlled release capsule dosage form prepared from the composition of claim 2.

11. A hydrodynamically balanced controlled release tablet dosage form prepared from the composition of claim 1.

12. A hydrodynamically balanced controlled release tablet dosage form prepared from the composition of claim 2.

13. A hydrodynamically balanced controlled release capsule dosage form prepared from the composition of claim 3.

14. A hydrodynamically balanced controlled release capsule dosage form prepared from the composition of claim 4.

15. A hydrodynamically balanced controlled release tablet dosage form prepared from the composition of claim 3.

16. A hydrodynamically balanced controlled release tablet dosage form prepared from the composition of claim 4.

17. A method for achieving desired high levels of L-Dopa in the blood of a subject which comprises orally administering to the subject the hydrodynamically balanced controlled release capsule of claim 9 containing the required amounts of L-Dopa and of decarboxylase inhibitor.

18. A method for achieving desired high levels of l-Dopa in the blood of a subject without undesirable side effects which comprises orally administering to the subject the hydrodynamically balanced controlled release capsule of claim 10 containing the required amounts of L-Dopa and of $N^1$-dl-seryl-$N^2$-(2,3,4-trihydroxybenzyl)hydrazine hydrochloride decarboxylase inhibitor.

19. A method for achieving desired levels of L-Dopa in the blood of a subject which comprises orally administering to the subject the hydrodynamically balanced controlled release tablet of claim 11 containing the required amounts of L-Dopa and decarboxylase inhibitor.

20. A method for achieving desired levels of l-Dopa in the blood of a subject which comprises orally administering to the subject the hydrodynamically balanced controlled release tablet of claim 12 containing the required amounts of L-Dopa and $N^1$-dl-seryl-$N^2$(2,3,4-trihydroxybenzyl)-hydrazine hydrochloride decarboxylase inhibitor.

* * * * *